United States Patent [19]

Middleton

[11] 4,141,895

[45] Feb. 27, 1979

[54] HYDROXYQUINAZOLINES AND THEIR USE AS INTERMEDIATES FOR PHARMACEUTICAL AGENTS

[75] Inventor: William J. Middleton, Chadds Ford, Pa.

[73] Assignee: E. I. Du Pont de Nemours and Company, Wilmington, Del.

[21] Appl. No.: 807,077

[22] Filed: Jun. 16, 1977

[51] Int. Cl.$^2$ ............... C07D 243/34; C07D 243/28; C07D 239/80

[52] U.S. Cl. .................. 260/239.3 D; 260/562 P; 260/562 B; 260/566 A; 260/566 R; 260/553 C; 260/544 Y; 424/244; 544/286; 562/605; 562/604

[58] Field of Search .............. 260/239.3 D, 251 QB

[56] References Cited

U.S. PATENT DOCUMENTS

3,440,281   4/1969   Fryer et al. .................. 260/239.3 D

FOREIGN PATENT DOCUMENTS

836768   6/1976   Belgium ........................ 260/239.3 D
2460360  6/1976   Fed. Rep. of Germany ... 260/239.3 D

OTHER PUBLICATIONS

Yamada et al., "Bull. Chem. Soc.," (Japan), vol. 47, pp. 343–347, (1974).

Bell et al., "J. Organic Chem.," vol. 27, pp. 562–566, (1962).

*Primary Examiner*—Natalie Trousof
*Assistant Examiner*—Robert T. Bond

[57] ABSTRACT

6-Substituted-2-halofluoromethyl-1,2-dihydro-2-hydroxy-1-methyl-4-phenylquinazolines and their use as intermediates in the preparation of 3-fluorobenzodiazepines, which are useful as tranquilizers, muscle relaxants and sedatives.

9 Claims, No Drawings

HYDROXYQUINAZOLINES AND THEIR USE AS INTERMEDIATES FOR PHARMACEUTICAL AGENTS

BACKGROUND OF THE INVENTION

Copending U.S. patent application Ser. No. 687,318, filed May 26, 1976 by Elena M. Bingham and William Joseph Middleton, which is a continuation-in-part of U.S. patent application Ser. No. 597,502, now abandoned, discloses certain novel 3-fluorobenzodiazepines of the formula:

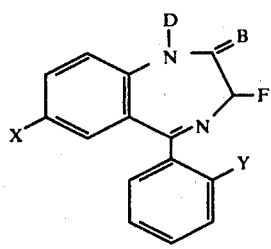

IV where
X is Cl, Br, $NO_2$, or $CF_3$;
Y is H, Cl, Br or F;
D is H, hydrocarbyl of 1–4 carbons, —$CH_2CF_3$, —CONHR, —$CH_2CH_2NR_2$, or —$CH_2CH_2NR_2\cdot A$, where R is alkyl of 1–4 carbons and A is a pharmaceutically suitable acid;
B is O; or
B and D together is =N—N=C(R')— where R' is H or $C_1$–$C_4$ alkyl,
and the use of such compounds as tranquilizers, muscle relaxants and sedatives in mammals. In addition, Bingham and Middleton disclose a process for making such compounds by reaction of the corresponding 3-hydroxybenzodiazepine with a dialkylaminosulfur trifluoride as follows:

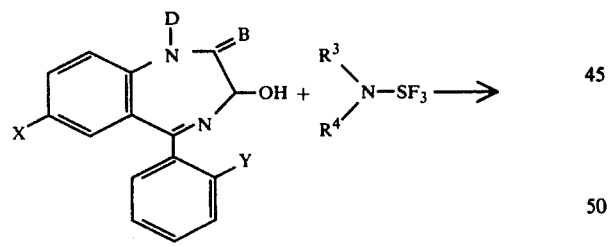

where $R^3$ and $R^4$ are a primary alkyl group of 1–4 carbons or taken together are —$(CH_2)_4$— or —$(CH_2)_5$.

In addition, copending U.S. patent applications Ser. Nos. 807,074; 807,075; and 807,076, filed simultaneously herewith together disclose an improved process for preparing such 3-fluorobenzodiazepines, which improved process can be summarized schematically as follows:

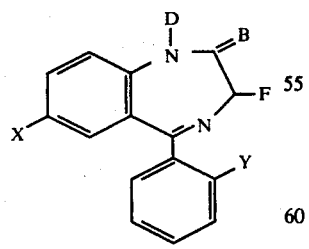

(1)

(2)

(3) and/or (4)

(3) + $R^2OH$ $\xrightarrow{\Delta}$ (5)

(6)

(3) and/or (4) and/or (6) + $NH_2OH \cdot A \longrightarrow$ (7)

(8)

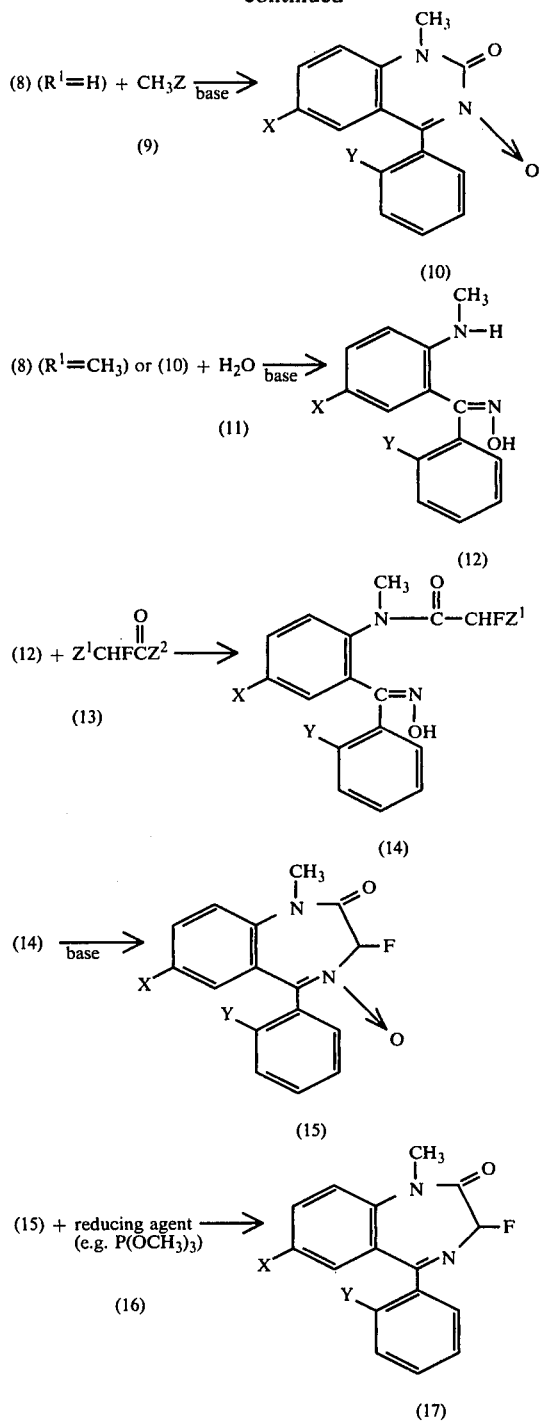

where
X is Br, Cl, NO$_2$ or CF$_3$;
Y is H, Br, Cl or F;
R is hydrocarbyl or halohydrocarbyl of 1-8 carbons;
R$^1$ is H or CH$_3$;
R$^2$ is alkyl of 1-6 carbons;
Z is I, Cl, Br, CF$_3$SO$_2$O—, FSO$_2$O—, CCl$_3$SO$_2$O— or CH$_3$OSO$_2$O—; and
Z$^1$ and Z$^2$ are Cl or Br.

SUMMARY OF THE PRESENT INVENTION

The present invention relates to an alternative process for making such 3-fluorobenzodiazepines, and to novel intermediates used in the alternative process.

More specifically, the present invention relates to
(a) a class of compounds of the formula:

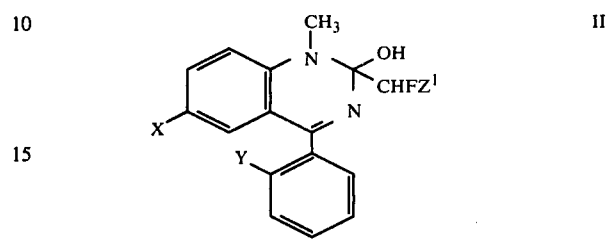

where
X is Cl, Br, NO$_2$ or CF$_3$;
Y is H, Cl, Br or F; and
Z$^1$ is Cl or Br;

(b) a process for preparing the compounds of formula II by reaction of a benzophenone imine of formula I with a halofluoroacetyl halide as follows:

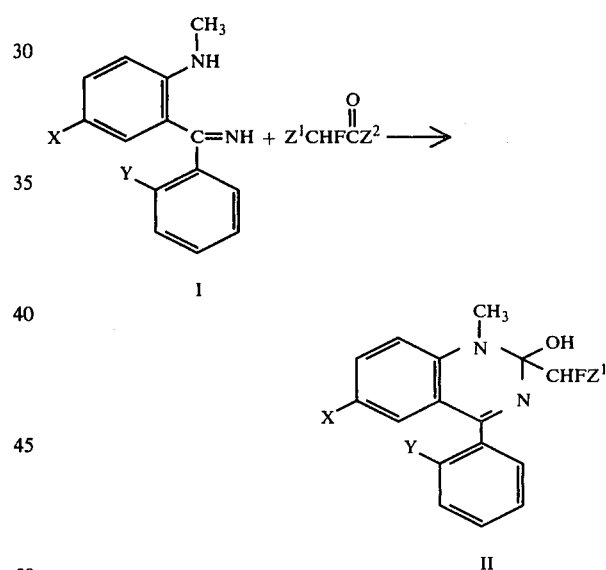

(c) a process for using the compounds of formula II as intermediates in the preparation of 3-fluorobenzodiazepines as follows:

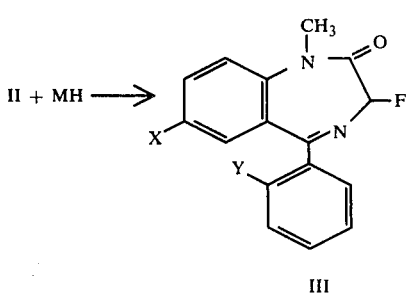

where M is an alkali metal.

DETAILED DESCRIPTION OF THE INVENTION

Preferred Compounds

Compounds from within the scope of U.S. patent application Ser. No. 687,318 which are preferred for their activity are those shown in formula IV, above, where, independently:

B = O;
X = Cl,
D = H;
D = $C_1$—$C_3$ alkyl;
X = Cl and D = H;
X = Cl and D = $C_1$-$C_3$ alkyl.

More preferred are those compounds where:
X = Cl or Br;
Y = H, Cl, or F;
D = H, —$CH_3$ or —$C_2H_5$; and
B = O.

Most preferred are those compounds where:
X = Cl or Br;
Y = H or F;
D = $CH_3$; and
B = O.

Necessarily, then, compounds of formula II which are preferred as intermediates are those where X is chlorine or bromine. More preferred compounds of formula II are those where X is chlorine or bromine and Y is hydrogen, chlorine or fluorine. Most preferred compounds are those where X is chlorine or bromine, Y is hydrogen or fluorine and $Z^1$ is chlorine.

Specifically preferred is the following compound: 6-chloro-2-chlorofluoromethyl-1,2-dihydro-2-hydroxy-1-methyl-4-phenylquinazoline.

Process Conditions

Starting material benzophenone imines of formula I can be prepared by treating benzophenone with ammonia as taught by Fryer and Sternbach in U.S. Pat. No. 3,440,281.

Benzophenone imines of Formula I can be converted to 3-fluorobenzodiazepines of Formula III by treatment with halofluoroacetyl halides and alkali metal hydrides in an inert solvent. The reaction may be conducted at a temperature of from −20° to 70°, but the preferred range is from 0° to 40° C. Solvents suitable for use are solvents that are inert to all of the reactants, and include ethers, such as tetrahydrofuran, diethyl ether, and ethylene glycol dimethyl ether, nitriles such as acetonitrile, and amides of secondary amines, such as dimethylformamide and dimethylacetamide. For best yields, at least two equivalents of an alkali metal hydride, such as sodium or potassium hydride, should be used. The product 3-fluorobenzodiazepines of Formula III can be isolated from the reaction mixture and purified by standard methods, such as crystallization and column chromatography.

Alternatively, the intermediate hydroxyquinazoline of Formula II can be prepared and isolated, and then be cyclized to a 3-fluorobenzodiazepine of Formula III in a separate step.

The hydroxyquinazolines of Formula II can be prepared by the reaction of a benzophenone imine of Formula I with a halofluoroacetyl halide in an inert solvent at a temperature of from 0° to 80°. A basic material can be present during the reaction or added afterwards to remove the hydrogen halide by-product. When an alkali metal hydride is used as the basic material, only one equivalent should be used. Other basic materials, such as tertiary amines (triethyl amine, pyridine, etc.) or inorganic bases such as alkali metal carbonates, bicarbonates, or hydroxides can also be used, either in equivalent amounts or in excess. The hydroxyquinazolines can be isolated from the reaction mixture and purified by standard methods.

The hydroxyquinazolines of Formula II can be converted to 3-fluorobenzodiazepines of Formula III by treatment with alkali metal hydrides in an inert solvent at a temperature of from 0° to 80°. Useful inert solvents are those previously described.

The following examples further illustrate the process of the present invention and the synthesis of the novel compounds of formula II. Parts are by weight and temperatures are in degrees Centigrade unless otherwise stated.

PREPARATION OF STARTING MATERIALS

Example 1

Part A. N-(2-Benzoyl-4-chlorophenyl)formamide

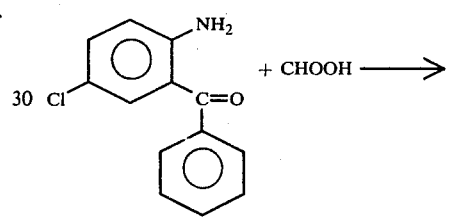

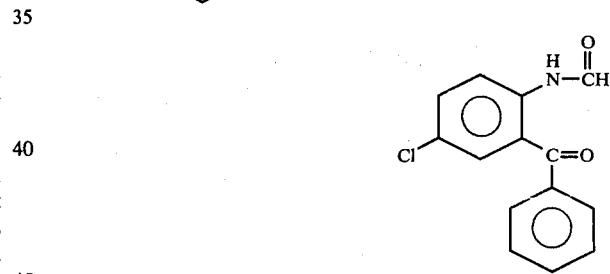

A mixture of 100 g (0.43 mole) of 2-amino-5-chlorobenzophenone and 500 g formic acid was refluxed for 1 hr, and then cooled and poured into 1 l. of ice water. The solid that precipitated was collected on a filter, washed with water, dried in air, and recrystallized from heptane-benzene to give 103.5 g (93%) of the formamide as colorless crystals, mp 89°–91°.

Part B.
N-Methyl-N-(2-benzoyl-4-chlorophenyl)formamide

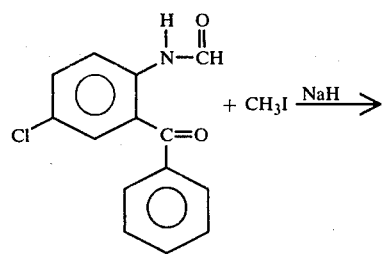

-continued

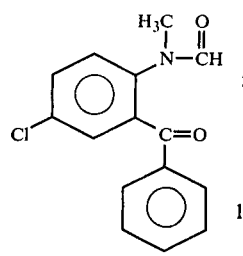

Sodium hydride (0.8 mole, 38.4 g of 50% in mineral oil) was added to a solution of 197.4 g (0.76 mole) of N-(2-benzoyl-4-chlorophenyl)formamide in 800 ml dimethylformamide. When the evolution of hydrogen ceased, 184 g of methyl iodide was added dropwise at such a rate that the temperature of the reaction mixture slowly rose to 70°. The reaction mixture was stirred for 90 min., and then poured into 2 l. of water. The aqueous mixture was extracted four times with 300 ml portions of methylene chloride, and the combined extracts were washed with water, dried (MgSO₄) and evaporated to dryness under reduced pressure. The residue was recrystallized from methanol to give 145.4 g (70% yield) of the N-methylformamide as colorless crystals: mp 93.5°–94.5°; $^1$H nmr (CDCl$_3$) showed two methyl peaks at $\delta$ 2.94 and 3.23 ppm (ratio 70:30).

Anal. Calcd for $C_{15}H_{12}ClNO_2$: C, 65.82; H, 4.42; N, 5.12. Found: C, 65.65; H, 4.52; N, 5.11.

Part C. 5-Chloro-2-(methylamino)benzophenone Imine

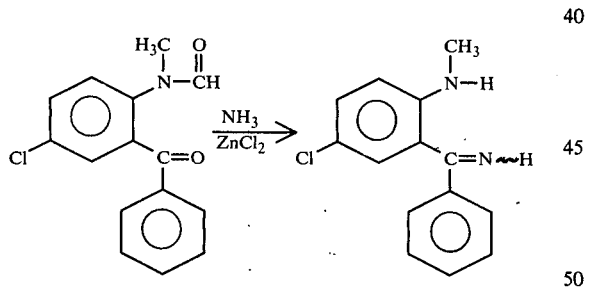

A mixture of 41.1 g (0.15 mole) of N-methyl-N-(2-benzoyl-4-chlorophenyl)formamide, 90 ml methanol, 90 g anhydrous ammonia, and 0.5 g zinc chloride was heated in a sealed 360 ml Hastelloy ® tube at 150° for 15 hr. and then cooled and vented. The solid portion of the residue was collected on a filter and recrystallized from methanol to give 27.8 g (76%) of 5-chloro-2-methylaminobenzophenone imine as long yellow needles: mp 93°–95°; $^1$H nmr (CDCl$_3$) $\delta$ 2.92 ppm (d, J = 5.5 Hz, 3H), 6.65 ppm (d, J = 9 Hz, 1H) 7.4 ppm (m, 7H) and 9.4 ppm (broad, 2NH).

Anal. Calcd for $C_{14}H_{13}ClN_2$: C, 68.71; H, 5.35; N, 11.45. Found: C, 69.00; H, 5.48; N, 11.37.

EXAMPLE 2

5-Chloro-2-methylaminobenzophenone Imine

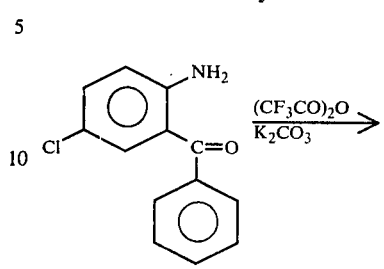

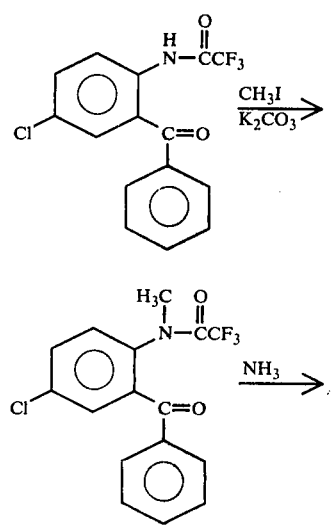

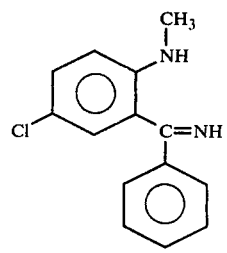

A mixture of 100 g of 2-amino-5-chlorobenzophenone, 250 g of potassium carbonate, and 500 ml acetonitrile were stirred together and 165 g of trifluoroacetic anhydride was added dropwise. The temperature rose spontaneously to 70°, and stirring was continued for one hour during which the mixture cooled to 40°. Methyl iodide (100 g) was added and the mixture was warmed to 70° with vigorous stirring. The temperature was held at 65°–70° for one hour, then filtered and the solvent evaporated. The residual oil was dissolved in ether and filtered. The ether was evaporated and the yellow oil (wt. 144 g) was dissolved in methanol (300 ml) and heated in a bomb with anhydrous ammonia (200 g) and ZnCl$_2$ (0.5 g). The yellow solid was filtered off and washed with water. Crystallization from methanol gave 64.7 g (61%) of 5-chloro-2-methylaminobenzophenone imine as yellow needles, mp 93°–95°.

EXAMPLE 3

Part A. Sodium Chlorofluoroacetate

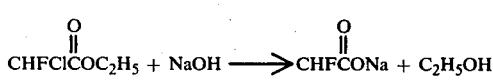

Eight hundred ml (4 mole) of 5N sodium hydroxide was added dropwise over a period of 30 min. to a stirred sample of 523.8 g (4.0 mole) of ethyl chlorofluoroacetate (prepared as described by B. Englund, "Organic Syntheses," Col. Vol. IV, p. 184, John Wiley and Sons, Inc., New York, 1963) contained in a 1-liter flask cooled in an ice bath. Stirring was continued until a homogenous solution was obtained (about 30 min.), and then the resulting solution was evaporated to dryness at 100° and under reduced pressure. The white residue was broken up and dried in a vacuum oven at 80° to give 504 g (94%) of sodium chlorofluoroacetate as a white crystalline powder.

Part B. Chlorofluoroacetyl Chloride

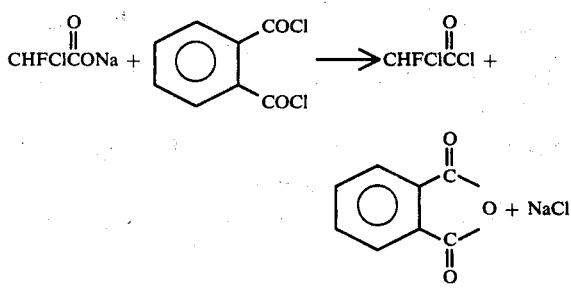

A 3-l., three-necked flask was fitted with a thermometer, a heating mantle, a mechanical stirrer, and a distillation head with a condenser and a 500 ml receiving flask backed up by a dry ice cooled trap. The reaction flask was charged with 500 g (3.72 mole) of crude sodium chlorofluoroacetate and 1 l. (1400 g, 6.9 mole) of practical grade phthaloyl chloride. The stirrer was started, and the contents of the flask were heated slowly until product began to distill from the reaction mixture (pot temperature about 100°-110°). The heating mantle was turned off until the initial reaction subsided, and then heating was resumed and continued until the pot temperature reached 245°. The distillate in the receiver and the dry ice cooled trap were combined (437 g, 90% crude yield) and redistilled through an 18 in. spinning band column to give 330.8 g (68%) of chlorofluoroacetyl chloride as a colorless liquid, bp 69°-69.5°. The fraction boiling between 65° and 69° was redistilled to give an additional 45.3 g (9.3%), which is a total yield of 376.1 g (77%) of product boiling at 69°-69.5°.

EXAMPLE 4

Part A. Sodium Bromofluoroacetate

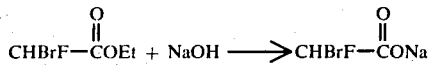

A solution of 40 g (1 mole) of sodium hydroxide in 100 ml water was added dropwise to a stirred suspension of 170 g (0.92 mole) of ethyl bromofluoroacetate in 250 ml water cooled to 20°. The reaction mixture was stirred for 2 hr, neutralized with hydrochloric acid, and evaporated to dryness under reduced pressure. There was obtained 158 g of the sodium salt as a white powder: mp 200° C. (dec.); $^{19}$F nmr (H$_2$O) δ −139.2 ppm (d, J = 52 Hz).

Part B. Bromofluoroacetyl Chloride

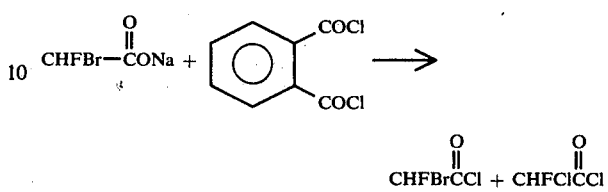

A stirred mixture of 158 g (0.88 mole) of crude sodium bromofluoroacetate and 343 g (1.68 mole) of phthaloyl chloride was heated together in a simple still until a product distilled out. Heating was continued until the reaction temperature reached 240° and no further distillate formed. The distillate was fractionated to give 31.4 g (27%) of chlorofluoroacetyl chloride as a colorless liquid, bp 68°-70°; and 42 g (27%) of bromofluoroacetyl chloride as a colorless liquid; bp 93°; $^1$H nmr (CCl$_3$F) δ 6.72 ppm (d, J = 51.5 Hz); $^{19}$F nmr (CCl$_3$F) δ −141.7 ppm (d, J = 51 Hz).

Anal. Calcd for C$_2$HBrClFO: C, 13.69; H, 0.58; F, 10.83. Found: C, 13.82; H, 0.83; F, 10.72.

SYNTHESIS OF COMPOUNDS OF FORMULA II

EXAMPLE 5

6-Chloro-2-chlorofluoromethyl-1,2-dihydro-2-hydroxy-1-methyl-4-phenylquinazoline

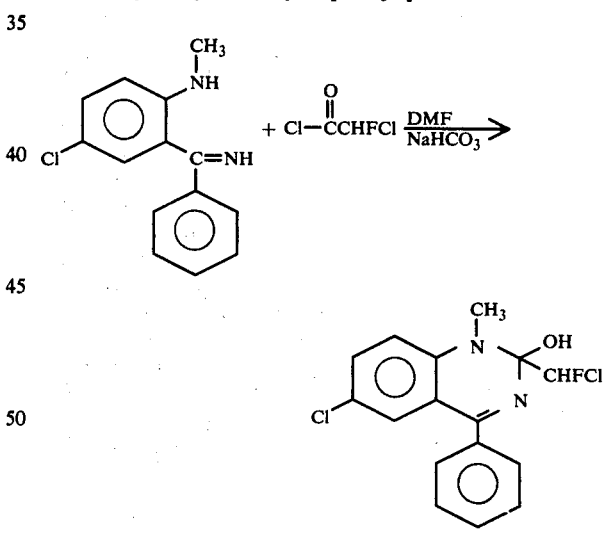

A 15.75-g (0.12 mole) sample of chlorofluoroacetyl chloride was added dropwise to 12.24 g (0.05 mole) of 5-chloro-2-methylaminobenzophenone imine in 100 ml of dimethylformamide at 25°-40°. The reaction mixture was stirred for 1 hr at 25° and then poured into 200 ml of 5% aqueous sodium bicarbonate solution. The solid that precipitated was collected on a filter, washed with water, and recrystallized from acetone to give 8.3 g (49%) of 6-chloro-2-chlorofluoromethyl-1,3-dihydro-2-hydroxy-1-methyl-4-phenylquinazoline as yellow needles: mp 115°-120° (dec.).

Recrystallization of material prepared in a similar manner from ethanol gave the reaction product. 6- chloro-2-chlorofluoromethyl-2-ethoxy-1,2-dihydro-1-methyl-4-phenylquinazoline (mixture of diastereoisomers) as yellow needles: mp 103°-104°.

Anal. Calcd for $C_{18}H_{17}Cl_2FN_2O$: C, 58.87; H, 4.67; F, 5.17; N, 7.63. Found: C, 58.82; H, 4.76; F, 5.08; N, 7.45.

EXAMPLE 6

6-Chloro-2-chlorofluoromethyl-1,2-dihydro-2-hydroxy-1-methyl-4-phenylquinazoline

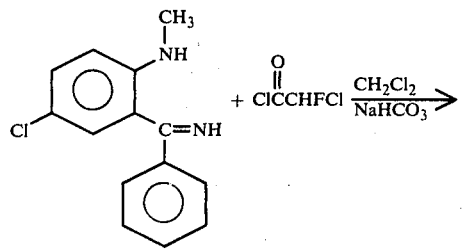

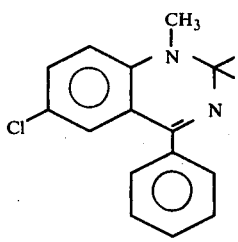

A solution of 7.2 g (0.055 mole) of chlorofluoroacetyl chloride in 15 ml of methylene chloride was added dropwise to a stirred solution of 12.24 g (0.05 mole) of 5-chloro-2-methylaminobenzophenone in 120 ml of methylene chloride containing 7.2 g (0.055 mole) of suspended sodium bicarbonate and cooled to 5°. The color turned deep red and then faded to light yellow. The reaction mixture was warmed to room temperature (25°) and stirred overnight (18 hr). Water, 100 ml, was added, and the organic layer was separated, dried (MgSO₄) and evaporated to dryness under reduced pressure. The residue was recrystallized from benzene to give 6.38 g of a mixture of the two diastereoisomers of 6-chloro-2-chlorofluoromethyl-1,2-dihydro-2-hydroxy-1-methyl-4-phenylquinazoline as yellow crystals: mp 121°-123° (dec.); ¹⁹F nmr (CDCl₃) δ −146.6 ppm (d, J = 50 Hz, 59%) and δ −148.7 ppm (d, J = 49 Hz, 41%).

Anal. Calcd for $C_{16}H_{13}Cl_2FN_2O$: C, 56.65; H, 3.86; F, 5.60; N, 8.26. Found: C, 56.70; H, 4.11; F, 5.57; N, 8.24.

EXAMPLE 7

6-Chloro-2-chlorofluoromethyl-1,2-dihydro-2-hydroxy-1-methyl-4-phenylquinazoline

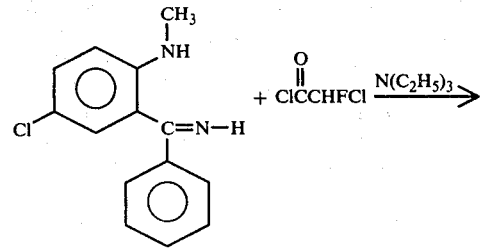

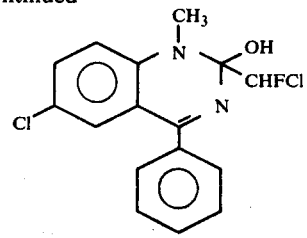

A solution of 6.55 g (0.05 mole) of chlorofluoroacetyl chloride in 50 ml of ether was added dropwise to a solution of 12.27 g (0.05 mole) of 5-chloro-2-methylaminobenzophenone imine and 5.06 g of triethylamine in 200 ml of ether cooled to 0°-5°. The reaction mixture was stirred for 2 hr at 0°-5°, and then poured into water. The organic layer was separated, washed with water, and then filtered to give 7.21 g of product. The ether filtrate was evaporated to dryness, and the residue was recrystallized from benzene to give an additional 1.07 g of product. All together, there was obtained 8.28 g of 6-chloro-2-chlorofluoromethyl-1,2-dihydro-2-hydroxy-1-methyl-4-phenylquinazoline (as a mixture of diastereoisomers). ¹⁹F nmr (DMSO-d₆) δ −142.2 ppm (d, J = 49 Hz, 55%) and δ −148.0 ppm (d, J = 48 Hz, 45%).

SYNTHESIS OF COMPOUNDS OF FORMULA III

EXAMPLE 8

7-Chloro-3-fluoro-1,3-dihydro-1-methyl-5-phenyl-2H-1,4-benzodiazepin-2-one

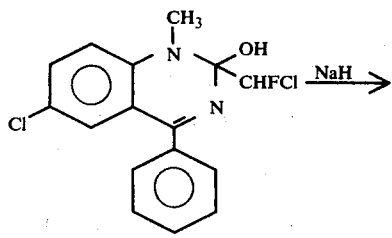

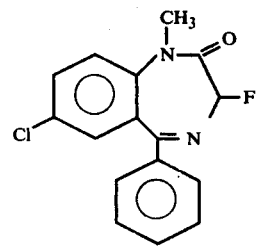

A solution of 1.70 g (5 mmole) of 6-chloro-2-chlorofluoromethyl-1,2-dihydro-2-hydroxy-1-methyl-4-phenylquinazoline in 25 ml tetrahydrofuran was cooled to 0°, and 0.15 g (6.2 mmole) of sodium hydride suspended in 5 ml of tetrahydrofuran was added. The reaction mixture was stirred for 2 hr at 0°, and then poured into 250 ml water. The aqueous mixture was extracted with methylene chloride, and the extracts were washed with water, dried (MgSO₄) and evaporated to dryness to give 1.4 g of a yellow residue.

Analysis indicated this residue contains 44.9% of the starting quinazoline and 15.1% of the product. The calculated yield of the reaction is 22% (14% conversion). The 7-chloro-3-fluoro-1,3-dihydro-1-methyl-5- phenyl-2H-1,4-benzodiazepin-2-one was isolated in pure form by column chromatography on silica gel, with cyclopentane as the eluting solvent. $^{19}$F nmr (CDCl$_3$) δ −161.7 ppm (d, J = 57 Hz).

EXAMPLE 9

7-Chloro-3-fluoro-1,3-dihydro-1-methyl-5-phenyl-2H-1,4-benzodiazepin-2-one

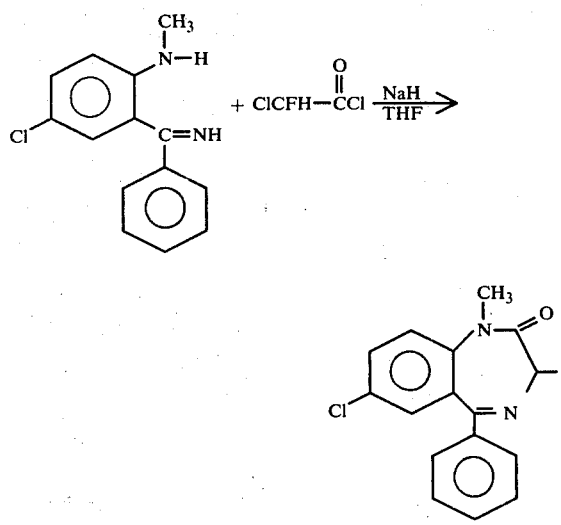

Sodium hydride (0.1 mole, from 5.0 g of 50% in oil, with oil washed out with tetrahydrofuran) was added to a stirred solution of 9.8 g (0.04 mole) of 5-chloro-2-methylaminobenzophenone imine in 200 ml of tetrahydrofuran. A 6.55-g (0.05 mole) sample of chlorofluoroacetyl chloride was then added at 25°–35°. The reaction mixture was stirred for 2 hr, and then poured into water. The aqueous mixture was extracted with methylene chloride, and the extracts were washed with water, dried (MgSO$_4$) and evaporated to dryness under reduced pressure to give 12.9 g of a dark, amorphous solid. Chromatographic analysis indicated this product is 24.4% starting material and 22.3% product. The calculated conversion to 7-chloro-3-fluoro-1,3-dihydro-1-methyl-5-phenyl-2H-1,4-benzodiazepin-2-one is 24%, and the yield is 34%. (Fluorine nmr same as for Example 8)

EXAMPLE 10

7-Chloro-3-fluoro-1,3-dihydro-1-methyl-5-phenyl-2H-1,4-benzodiazepin-2-one

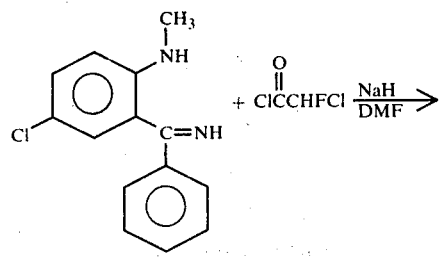

-continued

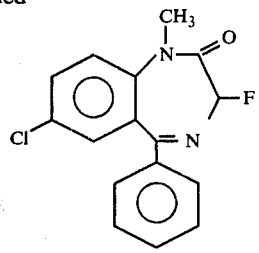

Sodium hydride (0.02 mole) was added to a solution of 4.9 g (0.02 mole) of 5-chloro-2-methylaminobenzophenone imine in 100 ml of dimethyl formamide. When the hydrogen evolution ceased, 3.27 g (0.025 mole) of chlorofluoroacetyl chloride was added dropwise at room temperature, and the reaction mixture was stirred for 2 hr, poured into cold water, neutralized with 10% hydrochloric acid, and extracted with methylene chloride. The extract was washed with water, dried (MgSO$_4$), and evaporated to dryness under reduced pressure to give 5.38 g of residue. Chromatographic analysis of the residue indicated it contained 43.3% of the starting imine, and 18.4% of product. The 7-chloro-3-fluoro-1,3-dihydro-1-methyl-5-phenyl-2H-1,4-benzodiazepin-2-one was isolated in pure form by column chromatography on silica gel, with cyclopentane as the eluting solvent. (Fluorine nmr same as for Example 8)

EXAMPLE 11

7-chloro-3-fluoro-1,3-dihydro-1-methyl-5-phenyl-2H-1,4-benzodiazepin-2-one

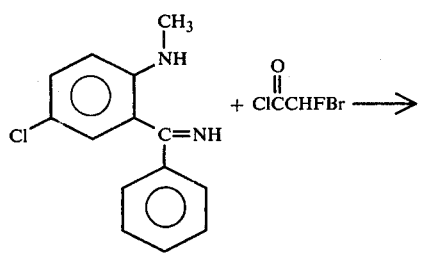

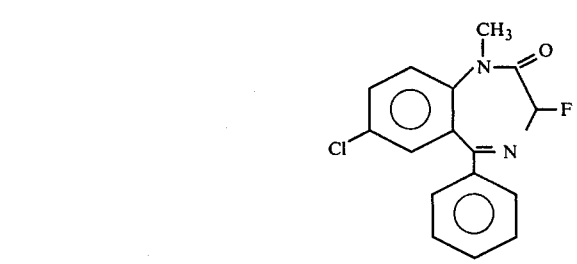

A suspension of 0.03 mole of sodium hydride in 10 ml of tetrahydrofuran was added to a solution of 2.45 g (0.01 mole) of 5-chloro-2-methylaminobenzophenone in 50 ml of tetrahydrofuran. When evolution of hydrogen ceased (after 1 hr), 2.3 g (0.013 mole) of bromofluoroacetyl chloride was added at 25°–30°, and the reaction mixture was stirred for 1 hr at room temperature. The mixture was poured into water and extracted with methylene chloride. The extracts were dried (MgSO$_4$) and evaporated to dryness to give a residue that contained about 20% 7-chloro-3-fluoro-1,3-dihydro-1-methyl-5-phenyl-2H-1,4-benzodiazepin-2-one. (Fluorine nmr same as for Example 8).

The following equations illustrate additional 3-fluorobenzodiazepines that can be prepared by the processes disclosed and illustrated above using benzophenone imines and a suitable halofluoroacetyl halide.

4. A compound of claim 2 where Y is hydrogen, chlorine or fluorine.

5. A compound of claim 2 where Y is hydrogen or fluorine.

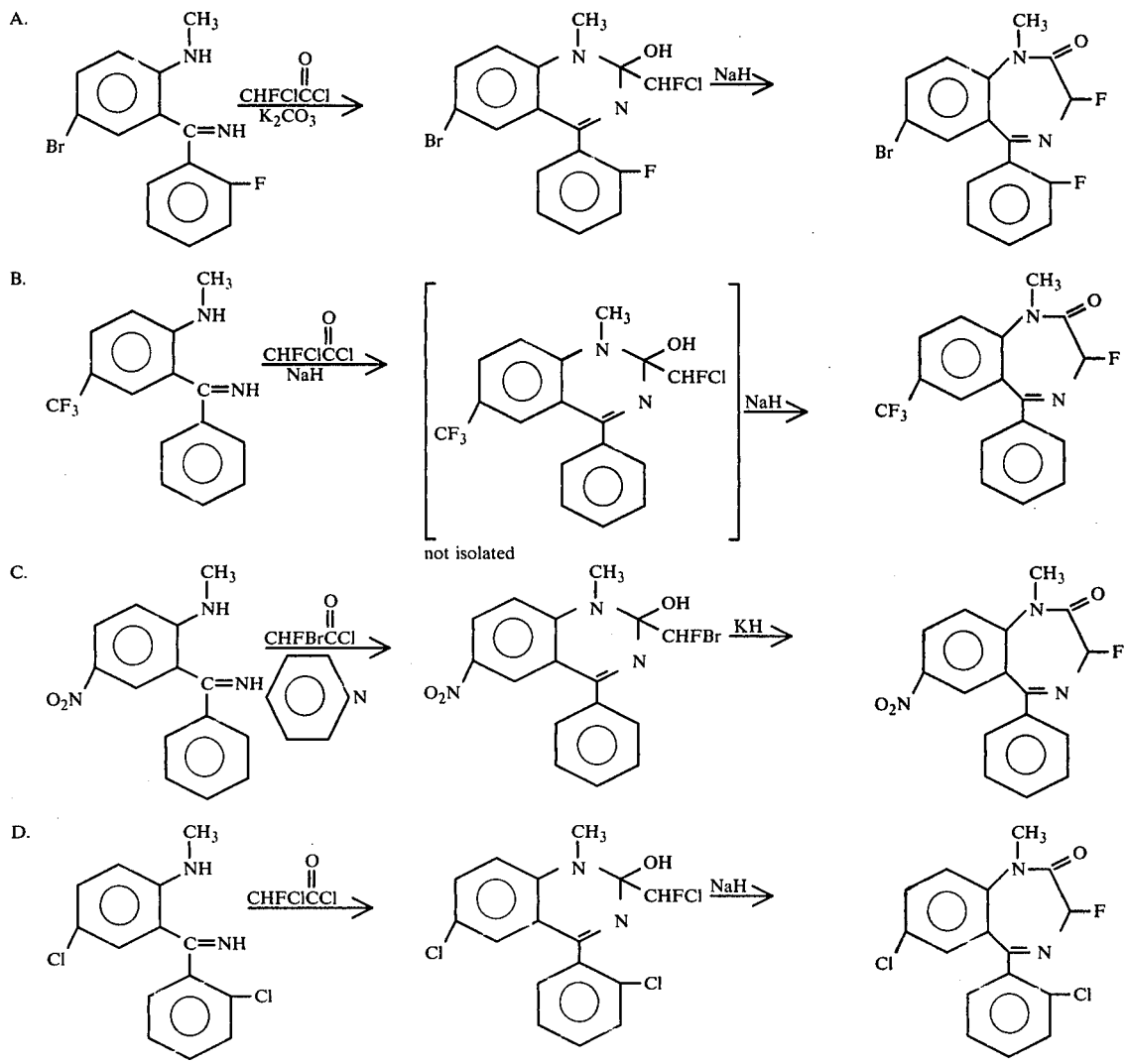

I claim:

1. A compound of the formula:

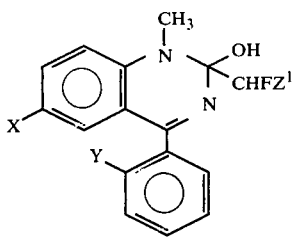

where
X is Cl, Br, NO₂, or CF₃;
Y is H, Br, Cl or F; and
Z¹ is Cl or Br.

2. A compound of claim 1 where X is chlorine or bromine.

3. A compound of claim 1 where Y is hydrogen, chlorine or fluorine.

6. The compound of claim 1 where X is chlorine, Y is hydrogen and Z¹ is chlorine.

7. A process for preparing a compound of the formula:

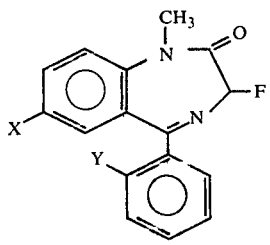

where
X is Cl, Br, NO₂ or CF₃; and
Y is H, Br, Cl or F;
which comprises reacting a compound of the formula:

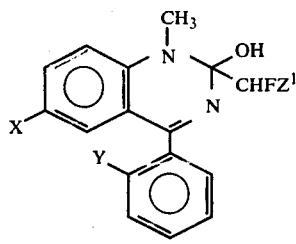

with an alkali metal hydride, where $Z^1$ is Cl or Br.

8. A process for preparing a compound of the formula:

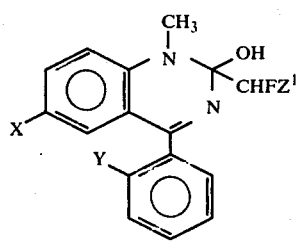

where
X is Cl, Br, $NO_2$ or $CF_3$;
Y is H, Br, Cl or F; and
$Z^1$ is Cl or Br;
which comprises reacting a compound of the formula:

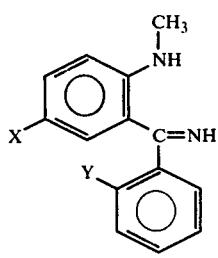

with a halofluoroacetyl halide of the formula

where $Z^1$ and $Z^2$ are Cl or Br.

9. A process for preparing a compound of the formula

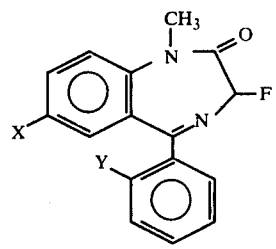

where
X is Cl, Br, $NO_2$ or $CF_3$; and
Y is H, Cl, Br, or F;
which comprises the following steps in sequence:
(a) reacting a compound of the formula

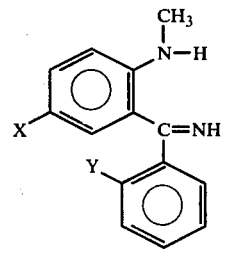

with a halofluoroacetyl halide of the formula

to produce a compound of the formula:

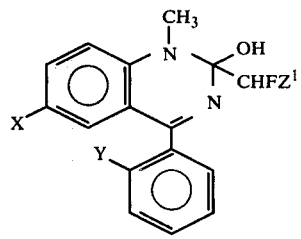

(b) reacting the reaction product of step (a) with an alkali metal hydride,
where $Z^1$ and $Z^2$ are Br or Cl.

* * * * *

UNITED STATES PATENT OFFICE
CERTIFICATE OF CORRECTION

PATENT NO. : 4141895

Page 1 of 2

DATED : 2/27/79

INVENTOR(S) : Middleton, William J.

It is certified that error appears in the above-identified patent and that said Letters Patent are hereby corrected as shown below:

The formula in Claim 1, the second formula in Claim 7, the first formula in Claim 8, and the last formula in Claim 9 should appear as follows:

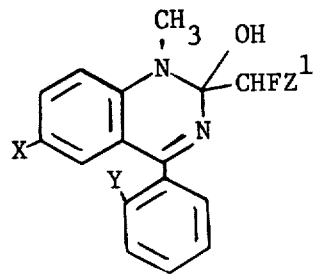

In Claims 7 and 9, the first formula should appear as follows:

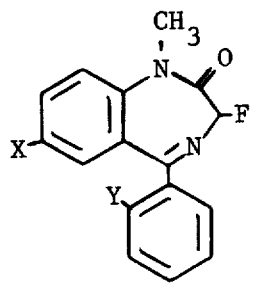

UNITED STATES PATENT OFFICE
CERTIFICATE OF CORRECTION

PATENT NO. : 4141895

DATED : 2/27/79

INVENTOR(S) : Middleton, William J.

It is certified that error appears in the above-identified patent and that said Letters Patent are hereby corrected as shown below:

In Claims 8 and 9, the second formula should appear as follows:

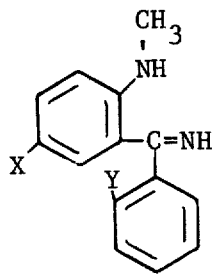

Signed and Sealed this

Thirtieth Day of October 1979

[SEAL]

Attest:

RUTH C. MASON
Attesting Officer

LUTRELLE F. PARKER
Acting Commissioner of Patents and Trademarks